United States Patent
Mamiya (10) Patent No.: US 10,215,556 B2
(45) Date of Patent: Feb. 26, 2019

(54) THREE-DIMENSIONAL MEASURING APPARATUS

(71) Applicant: Takahiro Mamiya, Aichi (JP)

(72) Inventor: Takahiro Mamiya, Aichi (JP)

(73) Assignee: CKD Corporation, Aichi (JP)

( * ) Notice: Subject to any disclaimer, the term of this patent is extended or adjusted under 35 U.S.C. 154(b) by 726 days.

(21) Appl. No.: 14/085,834

(22) Filed: Nov. 21, 2013

(65) Prior Publication Data

US 2014/0078296 A1    Mar. 20, 2014

Related U.S. Application Data

(63) Continuation of application No. PCT/JP2011/066816, filed on Jul. 25, 2011.

(30) Foreign Application Priority Data

May 31, 2011    (JP) ................................. 2011-121190

(51) Int. Cl.
*G01B 11/06* (2006.01)
*G01N 21/88* (2006.01)
(Continued)

(52) U.S. Cl.
CPC .......... *G01B 11/25* (2013.01); *G01B 11/0608* (2013.01); *G01B 11/2513* (2013.01);
(Continued)

(58) Field of Classification Search
None
See application file for complete search history.

(56) References Cited

U.S. PATENT DOCUMENTS

| 2002/0039187 A1* | 4/2002 | Keranen | ............ G01B 11/2522 356/604 |
| 2003/0039388 A1* | 2/2003 | Ulrich | ................ G01B 11/2513 382/145 |

(Continued)

FOREIGN PATENT DOCUMENTS

| JP | 11-211433 A | 8/1999 |
| JP | 2003-279334 A | 10/2003 |

(Continued)

OTHER PUBLICATIONS

International Search Report in corresponding International Application No. PCT/JP2011/066816 dated Aug. 23, 2011 (4 pages).

*Primary Examiner* — Mohammed S Rahaman
(74) *Attorney, Agent, or Firm* — Osha Liang LLP (57) ABSTRACT

A three-dimensional measuring apparatus includes a first irradiating unit, a second irradiating unit, imaging unit that can image a measured object, a first image data acquiring unit that acquires a plurality of image data imaged by the imaging unit under the light pattern irradiated from the first irradiating unit for each predetermined amount of conveyance by the measured object, a three-dimensional measuring unit that three dimensionally measures based on a plurality of image data acquired by the first image data acquiring unit, and a second image data acquiring unit that acquires image data imaged by the imaging unit under the second light irradiated from the second irradiating unit between after predetermined image data from among the plurality of image data acquired by the first image data acquiring unit is imaged and until the next image data is imaged.

10 Claims, 7 Drawing Sheets

(51) Int. Cl.
*G01B 11/25* (2006.01)
*G01N 21/956* (2006.01)
*G06T 7/521* (2017.01)
*G06T 7/586* (2017.01)

(52) U.S. Cl.
CPC .......... *G01N 21/956* (2013.01); *G06T 7/521* (2017.01); *G06T 7/586* (2017.01); *G01N 21/95684* (2013.01); *G01N 2021/8829* (2013.01); *G01N 2021/95638* (2013.01); *G06T 2207/10024* (2013.01); *G06T 2207/10152* (2013.01); *G06T 2207/30141* (2013.01)

(56) References Cited

U.S. PATENT DOCUMENTS

| | | | | |
|---|---|---|---|---|
| 2010/0066824 A1* | 3/2010 | Burton | ............... | B26D 7/30 |
| | | | | 348/89 |
| 2011/0050859 A1* | 3/2011 | Kimmel | ............ | G01B 11/2509 |
| | | | | 348/50 |
| 2012/0188354 A1* | 7/2012 | Munro | ................ | H04N 5/332 |
| | | | | 348/77 |

FOREIGN PATENT DOCUMENTS

| | | |
|---|---|---|
| JP | 2005-140537 A | 6/2005 |
| JP | 2006-227652 A | 8/2006 |
| JP | 2006-300539 A | 11/2006 |

\* cited by examiner

| Time ↓ | Types of Irradiated Light | | P17 | P16 | P15 | P14 | P13 | P12 | P11 | P10 | P9 | P8 | P7 | P6 | P5 | P4 | P3 | P2 | P1 |
|---|---|---|---|---|---|---|---|---|---|---|---|---|---|---|---|---|---|---|---|
| t1 | First luminance light pattern | Coordinates | P17 | P16 | P15 | P14 | P13 | P12 | P11 | P10 | P9 | P8 | P7 | P6 | P5 | P4 | P3 | P2 | P1 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t2 | First luminance red light | Coordinates | P18 | P17 | P16 | P15 | P14 | P13 | P12 | P11 | P10 | P9 | P8 | P7 | P6 | P5 | P4 | P3 | P2 |
| | | Color | R | R | R | R | R | R | R | R | R | R | R | R | R | R | R | R | R |
| t3 | Second luminance light pattern | Coordinates | P19 | P18 | P17 | P16 | P15 | P14 | P13 | P12 | P11 | P10 | P9 | P8 | P7 | P6 | P5 | P4 | P3 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t4 | Second luminance red light | Coordinates | P20 | P19 | P18 | P17 | P16 | P15 | P14 | P13 | P12 | P11 | P10 | P9 | P8 | P7 | P6 | P5 | P4 |
| | | Color | r | r | r | r | r | r | r | r | r | r | r | r | r | r | r | r | r |
| t5 | First luminance light pattern | Coordinates | P21 | P20 | P19 | P18 | P17 | P16 | P15 | P14 | P13 | P12 | P11 | P10 | P9 | P8 | P7 | P6 | P5 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t6 | First luminance green light | Coordinates | P22 | P21 | P20 | P19 | P18 | P17 | P16 | P15 | P14 | P13 | P12 | P11 | P10 | P9 | P8 | P7 | P6 |
| | | Color | G | G | G | G | G | G | G | G | G | G | G | G | G | G | G | G | G |
| t7 | Second luminance light pattern | Coordinates | P23 | P22 | P21 | P20 | P19 | P18 | P17 | P16 | P15 | P14 | P13 | P12 | P11 | P10 | P9 | P8 | P7 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t8 | Second luminance green light | Coordinates | P24 | P23 | P22 | P21 | P20 | P19 | P18 | P17 | P16 | P15 | P14 | P13 | P12 | P11 | P10 | P9 | P8 |
| | | Color | g | g | g | g | g | g | g | g | g | g | g | g | g | g | g | g | g |
| t9 | First luminance light pattern | Coordinates | P25 | P24 | P23 | P22 | P21 | P20 | P19 | P18 | P17 | P16 | P15 | P14 | P13 | P12 | P11 | P10 | P9 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t10 | First luminance blue light | Coordinates | P26 | P25 | P24 | P23 | P22 | P21 | P20 | P19 | P18 | P17 | P16 | P15 | P14 | P13 | P12 | P11 | P10 |
| | | Color | B | B | B | B | B | B | B | B | B | B | B | B | B | B | B | B | B |
| t11 | Second luminance light pattern | Coordinates | P27 | P26 | P25 | P24 | P23 | P22 | P21 | P20 | P19 | P18 | P17 | P16 | P15 | P14 | P13 | P12 | P11 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t12 | Second luminance blue light | Coordinates | P28 | P27 | P26 | P25 | P24 | P23 | P22 | P21 | P20 | P19 | P18 | P17 | P16 | P15 | P14 | P13 | P12 |
| | | Color | b | b | b | b | b | b | b | b | b | b | b | b | b | b | b | b | b |
| t13 | First luminance light pattern | Coordinates | P29 | P28 | P27 | P26 | P25 | P24 | P23 | P22 | P21 | P20 | P19 | P18 | P17 | P16 | P15 | P14 | P13 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t14 | | | | | | | | | | | | | | | | | | | |
| t15 | Second luminance light pattern | Coordinates | P31 | P30 | P29 | P28 | P27 | P26 | P25 | P24 | P23 | P22 | P21 | P20 | P19 | P18 | P17 | P16 | P15 |
| | | Phase of Bands | 0° | 22.5° | 45° | 67.5° | 90° | 112.5° | 135° | 157.5° | 180° | 202.5° | 225° | 247.5° | 270° | 292.5° | 315° | 337.5° | 360° |
| t16 | | | | | | | | | | | | | | | | | | | |

[FIG 6]

| | | P17 | P16 | P15 | P14 | P13 | P12 | P11 | P10 | P9 | P8 | P7 | P6 | P5 | P4 | P3 | P2 | P1 |
|---|---|---|---|---|---|---|---|---|---|---|---|---|---|---|---|---|---|---|
| First luminance light pattern | Coordinates | | | | | | | | | | | | | | | | | |
| | Phase of Bands | | | | | | | | | | | | | | | | 337.5° | 360° |
| First luminance red light | Coordinates | | | | | | | | | | | | | | | | P2 | ... |
| | Color | | | | | | | | | | | | | | | | R | |
| Second luminance light pattern | Coordinates | | | | | | | | | | | | | | | P3 | | |
| | Phase of Bands | | | | | | | | | | | | | | | 315° | | |
| Second luminance red light | Coordinates | | | | | | | | | | | | | | P4 | P3 | | |
| | Color | | | | | | | | | | | | | | R | R | | |
| First luminance light pattern | Coordinates | | | | | | | | | | | | | | P4 | | | |
| | Phase of Bands | | | | | | | | | | | | | | 337.5° | | | |
| First luminance green light | Coordinates | | | | | | | | | | | | | P5 | P4 | | | |
| | Color | | | | | | | | | | | | | r | r | | | |
| Second luminance light pattern | Coordinates | | | | | | | | | | | | | P5 | | | | |
| | Phase of Bands | | | | | | | | | | | | | 360° | | | | |
| Second luminance green light | Coordinates | | | | | | | | | | | | P6 | P5 | | | | |
| | Color | | | | | | | | | | | | G | r | | | | |
| First luminance light pattern | Coordinates | | | | | | | | | | | | P6 | | | | | |
| | Phase of Bands | | | | | | | | | | | | 337.5° | | | | | |
| First luminance blue light | Coordinates | | | | | | | | | | | P7 | P6 | | | | | |
| | Color | | | | | | | | | | | G | G | | | | | |
| Second luminance light pattern | Coordinates | | | | | | | | | | | P7 | | | | | | |
| | Phase of Bands | | | | | | | | | | | 360° | | | | | | |
| Second luminance blue light | Coordinates | | | | | | | | | | P8 | P7 | | | | | | |
| | Color | | | | | | | | | | g | G | | | | | | |

(Table continues — additional rows P8 through P31 with phase values 22.5°, 45°, 67.5°, 90°, 112.5°, 135°, 157.5°, 180°, 202.5°, 225°, 247.5°, 270°, 292.5°, 315°, 337.5°, 360° and color codes R, r, G, g, B, b forming the staircase pattern shown in the figure.)

[FIG 7]

| | | P31 | P30 | P29 | P28 | P27 | P26 | P25 | P24 | P23 | P22 | P21 | P20 | P19 | P18 | P17 | P16 | P15 | P14 | P13 | P12 |
|---|---|---|---|---|---|---|---|---|---|---|---|---|---|---|---|---|---|---|---|---|---|
| First Group Data | First Time (θ+0°) | | | | | | | | | | | | | | ... | 0° | ... | | | | |
| | Second Time (θ+90°) | | | | | | | | | | | | | | ... | 90° | ... | | | | |
| | Third Time (θ+180°) | | | | | | | | | | | | | | ... | 180° | ... | | | | |
| | Fourth Time (θ+270°) | | | | | | | | | | | | | | ... | 270° | ... | | | | |
| Second Group Data | First Time (θ+0°) | | | | | | | | | | | | | | ... | 45° | ... | | | | |
| | Second Time (θ+90°) | | | | | | | | | | | | | | ... | 135° | ... | | | | |
| | Third Time (θ+180°) | | | | | | | | | | | | | | ... | 225° | ... | | | | |
| | Fourth Time (θ+270°) | | | | | | | | | | | | | | ... | 315° | ... | | | | |
| Third Group Data | Red | | | | | | | | | | | | | | ... | R | ... | | | | |
| | Green | | | | | | | | | | | | | | ... | G | ... | | | | |
| | Blue | | | | | | | | | | | | | | ... | B | ... | | | | |
| Fourth Group Data | Red | | | | | | | | | | | | | | ... | r | ... | | | | |
| | Green | | | | | | | | | | | | | | ... | g | ... | | | | |
| | Blue | | | | | | | | | | | | | | ... | b | ... | | | | |

THREE-DIMENSIONAL MEASURING APPARATUS

CROSS-REFERENCE TO RELATED APPLICATIONS

This application is a continuation application of International Patent Application No. PCT/JP2011/0066816 filed on Jul. 25, 2011, which claims priority to Japanese Patent Application No. 2011-121190 filed on May 31, 2011 in Japan.

BACKGROUND OF INVENTION

Field of the Invention

The present invention relates to a three-dimensional measuring apparatus.

Background Art

Generally, when electronic components are mounted onto a printed substrate, cream solder is first printed on a predetermined electrode pattern disposed on the printed substrate. Next, the electronic component is provisionally set on the printed substrate according to the viscosity of the cream solder. Thereafter, soldering is performed by putting the printed substrate into a reflow furnace and performing a predetermined reflow process. Recently, an inspection of the printed state of the cream solder is required as a prior step to introducing into the reflow furnace, and a three-dimensional measuring apparatus is used in the inspection.

In recent years, proposals have been made for a variety of three-dimensional measuring apparatuses including those known as a non-contact type which uses light, and technology that relates to, for example, a three-dimensional measuring apparatus that uses a phase shift method is proposed.

Three-dimensional measuring apparatuses that use a phase shift method irradiate a light pattern having a sinusoidal (banded) light intensity distribution by irradiating unit made by combining a light source with a filter having a sine wave pattern. Further, observing is done using an imaging unit disposed directly above a point on the substrate. A CCD camera or the like made up of a lens, an imaging element, and the like may be used as the imaging unit. In this case, the light intensity I is given according to the below equation for the measuring point P on the screen.

$$I = B + A \cdot \cos \varphi$$

[Where B is direct current optical noise (offset component), A is a contrast of a sine wave (reflectance ratio), and $\varphi$ is a phase given due to the unevenness of the object]

At this time, the light pattern is moved to change the phase in, for example, four steps ($\varphi+0$, $\varphi+\pi/2$, $\varphi+\pi$, and $\varphi+3\pi/2$), and images that have intensity distributions I1, I2, I3, and I4 that correspond to these are incorporated to obtain the modulated portion (position information for driving height) $\theta$ based on the equation given below.

$$\theta = \arctan\{(I4-I2)/(I1-I3)\}$$

Using this modulated portion $\theta$, the three-dimensional coordinates (X, Y, Z) for the measuring point P can be found for the cream solder on the printed substrate, and the three-dimensional shape, particularly the height, of the measuring target can be measured.

In recent years, various technologies have been proposed (for example, see Patent Documents 1 and 2) where, in order to improve measurement accuracy, in addition to acquiring one set of image data (for example, four image data) for conventional three-dimensional measuring as described above, image data imaged under a different irradiating light than the light pattern used at the time of imaging the one set of image data is acquired separately.

PATENT DOCUMENTS

Patent Document 1: Japanese Unexamined Patent Application No. 2003-279334

Patent Document 2: Japanese Unexamined Patent Application No. 2006-300539

However, conventional technology disclosed in Patent Documents 1, 2 and the like, configures a predetermined measurement target scope (imaging scope) where after one set of image data is all imaged for use in three-dimensional measuring under a predetermined optical pattern, the measurement target scope undertakes separate imaging under a different irradiating light than the light pattern.

Therefore, in the conventional technology, there is a risk of extending the time beyond what is conventionally required to acquire all image data that pertains to a predetermined measurement target scope by that portion of separate imaging. Further, when multiple measurement target scopes are set on a single printed substrate, there is a risk that the time required for measuring a single printed substrate may be increased remarkably.

Note that the problems described above are not necessarily limited to measuring a height of a cream solder or the like printed on a printed substrate or to measurements according to a phase shift method but are also intrinsic to fields of other three-dimensional measuring apparatuses.

SUMMARY OF INVENTION

In light of the circumstances given above, an aspect of the present invention is to provide a three-dimensional measuring apparatus that can improve, or the like, measurement accuracy as well as suppress reduction in measurement efficiency while performing three-dimensional measurement.

Descriptions will be given hereinafter of separate means for resolving the problems described above in accordance with one or more embodiments of the present invention. Note that unique effects are given for corresponding means as necessary.

In one or more embodiments of the invention, a three-dimensional measuring apparatus includes a first irradiating unit that can irradiate a light pattern, onto a continuously conveyed measured object, having a banded light intensity distribution in a conveying direction of the measured object; second irradiating unit that can irradiate a second light that differs from the first light pattern, onto the measured object; imaging unit that can image the measured object irradiated by the various light; first image data acquiring unit that acquires a plurality of image data imaged by the imaging unit under the light pattern irradiated from the first irradiating unit for each predetermined amount of conveyance by the measured object; three-dimensional measuring unit that three dimensionally measures based on a plurality of image data acquired by at least the first image data acquiring unit; second image data acquiring unit that acquires image data imaged by the imaging unit under the second light irradiated from the second irradiating unit between after predetermined image data from among the plurality of image data acquired by the first image data acquiring unit is imaged and until the next image data is imaged; and specific process executing unit that executes a predetermined process based on image data acquired by the second image data acquiring unit. The second irradiating unit is configured as the second light that can irradiate a uniform light of a constant light intensity.

According to the above embodiments of the invention, a light pattern having a banded light intensity distribution is irradiated onto a continuously conveyed measured object, and the measured object that has been irradiated by the light pattern is imaged by the imaging unit for each predetermined amount of conveyance (for example, a distance equivalent to a phase $\pi/2$ of the light pattern). Accordingly, a plurality of image data is acquired for phases of the irradiated light pattern that differ by predetermined amounts (for example, by $\pi/2$ each). Further, a three-dimensional measurement can be taken for the measured object based on this image data.

In addition, in the above embodiments, imaging of the measured object under the second light irradiated from the second irradiating unit occurs during the time that a plurality of imaging times, which is the object of three-dimensional measuring, is performed. In other words, in addition to acquiring image data for three-dimensional measuring, all the image data required for performing three-dimensional measuring is acquired without extending the required time, and image data used for other purposes different from three-dimensional measuring (image data for executing the predetermined process according to the specific process executing unit) can be acquired separately.

As a result, combining a plurality of various types of measurements is made possible when performing three-dimensional measuring, and suppression of a reduction in measurement efficiency as well as improving, and the like, of measurement accuracy can be achieved.

In one or more embodiments of the invention, a three-dimensional measuring apparatus includes first irradiating unit that can irradiate a light pattern, onto a continuously conveyed measured object, having a banded light intensity distribution in a conveying direction of the measured object; second irradiating unit that can irradiate a second light that differs from the first light pattern, onto the measured object; imaging unit that can image the measured object irradiated by the various light; first image data acquiring unit that acquires a plurality of image data imaged by the imaging unit under the light pattern irradiated from the first irradiating unit for each predetermined amount of conveyance by the measured object; three-dimensional measuring unit that uses a phase shift method to three dimensionally measure based on a plurality of image data acquired by at least the first image data acquiring unit; second image data acquiring unit that acquires image data imaged by the imaging unit under the second light irradiated from the second irradiating unit between after predetermined image data from among the plurality of image data acquired by the first image data acquiring unit is imaged and until the next image data is imaged; and specific process executing unit that executes a predetermined process based on image data acquired by the second image data acquiring unit. The second irradiating unit is configured as the second light that can irradiate a uniform light of a constant light intensity.

According to the above embodiments of the invention, a light pattern having a banded light intensity distribution is irradiated onto a continuously conveyed measured object, and the measured object that has been irradiated by the light pattern is imaged by the imaging unit for each predetermined amount of conveyance (for example, a distance equivalent to a phase $\pi/2$ of the light pattern). Accordingly, a plurality of image data is acquired for phases of the irradiated light pattern that differ by predetermined amounts (for example, by $\pi/2$ each). Further, a three-dimensional measurement can be taken for the measured object according to a phase shift method based on this image data.

In addition, in the above embodiments, imaging of the measured object under the second light irradiated from the second irradiating unit occurs during the time that a plurality of imaging times, which is the object of three-dimensional measuring, is performed according to the phase shift method. In other words, in addition to acquiring image data for three-dimensional measuring, all the image data required for performing three-dimensional measuring according to the phase shift method is acquired without extending the required time, and image data used for other purposes different from three-dimensional measuring (image data for executing the predetermined process according to the specific process executing unit) can be acquired separately.

As a result, combining a plurality of various types of measurements is made possible when performing three-dimensional measuring using a phase shift method, and suppression of a reduction in measurement efficiency as well as improving, and the like, of measurement accuracy can be achieved.

In one or more embodiments of the invention, in the three-dimensional measuring apparatus according to any of the embodiments of the claimed invention, as described above, the second irradiating unit is configured as the second light that can irradiate by switching a plurality of various types of lights during the time until a plurality of imaging data acquired by the first image data acquiring unit is all imaged.

According to the above embodiments of the invention, image data for use in a plurality of types of uses can be acquired separately, and the effect given in the first unit and the like can be further enhanced. Here, a plurality of various types of light includes, of course, various lights having different irradiation modes such as uniform light and patterned light to be described hereinafter, and also includes similar types of light having different luminance such as, for example, two types of uniform light having different luminance.

Note that irradiating a plurality of different types of light having different luminance can suppress the occurrence of various types of problems that are based on differences in light and dark areas on the measured object.

For example, there are various colors in the surrounding area (hereinafter referred to as the background region) of the printed portion of the cream solder on the printed substrate as the measured object. This is because various colors are used in the glass epoxy resin and the resist film. Further, in a background region having a comparatively dark color such as, for example, black, the contrast of the image data tends to be smaller based on imaging by the imaging unit. In other words, there is a smaller difference between light and dark (luminance difference) in the light pattern on the image data. Therefore, there is a risk that measuring the height of the background region may become difficult. Normally, it would be preferable to adopt a height standard in the substrate in order to measure the height of the cream solder printed on the substrate to a more accurate degree. However, because the background region cannot be suitably used as a height reference plane, a problem may occur in which such height standard cannot be adopted for the substrate.

Accordingly, for example, switching the luminance of irradiated light to separately perform imaging according to a luminance suited to the solder print region (bright portion) and imaging according to a luminance suited to the background region (dark portion), and then appropriately measuring the height standard allows the generation of the problems described above to be suppressed.

In one or more embodiments of the invention, in the three-dimensional measuring apparatus according to any of the embodiments of the claimed invention, as described above, the second irradiating unit is configured as the second light that can irradiate a uniform light of a constant light intensity.

According to the above embodiments of the invention, luminance image data can be acquired. Therefore, based on the luminance image data, the three-dimensional data obtained by, for example, the three-dimensional measurement described above, can be mapped and the measurement region can be extracted, and the like, thereby enabling measurement accuracy to be further improved.

In one or more embodiments of the invention, in the three-dimensional measuring apparatus according to any of the embodiments of the claimed invention, as described above, the second irradiating unit is configured as the second light that can irradiate a light pattern having a banded light intensity distribution in a conveying direction of the measured object.

According to the above embodiments of the claimed invention, a light pattern that differs from the light pattern of the first irradiating unit (for example, a light pattern having a different luminance) can be irradiated. As a result, the three-dimensional measurements separate from the three-dimensional measurements described above can be newly performed to thereby further improve measurement accuracy.

In one or more embodiments of the invention, the three-dimensional measuring apparatus according to any of the embodiments of the claimed invention, as described above, further includes positioning unit for aligning coordinates between mutual image data acquired respectively at different positions in a conveying direction of the printed substrate.

According to the above embodiments, measurement efficiency can be improved and the like because various image data can be acquired without stopping the conveyance of the printed substrate.

Other aspects and advantages of the invention will be apparent from the following description and the appended claims.

BRIEF DESCRIPTION OF DRAWINGS

FIG. 6 is a table schematically illustrating when coordinate positions of a plurality of image data are aligned.

DETAILED DESCRIPTION

One or more embodiments of the invention will be described hereinafter with reference to drawings. First, a detailed description will be given of a configuration of the printed substrate used as the measured object.

Figure 2:
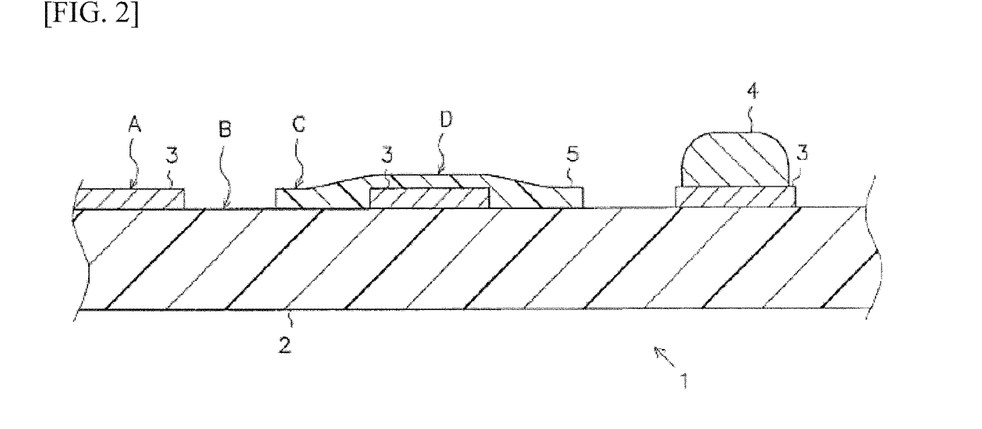
FIG. 2 is a cross-sectional view of a printed substrate.

As illustrated in FIG. 2, the printed substrate 1 forms a plate like shape and is provided with a base substrate 2 made up of glass epoxy resin and the like and an electrode pattern 3 made up of copper foil. Cream solder 4 is print formed on the predetermined electrode pattern 3. The region where the cream solder 4 is printed is referred to as the "solder print region." Portions other than the solder print region will be referred to comprehensively as the "background region," and this background region includes a region where the electrode pattern 3 is exposed (symbol A), a region where the base substrate 2 is exposed (symbol B), a region where a resist film 5 is coated on the base substrate 2 (symbol C), and a region where the resist film 5 is coated on the electrode pattern 3 (symbol D). Note that the resist film 5 has a coating on the printed substrate 1 so that the cream solder 4 does not get on portions other than a predetermined wiring portion.

Figure 1:
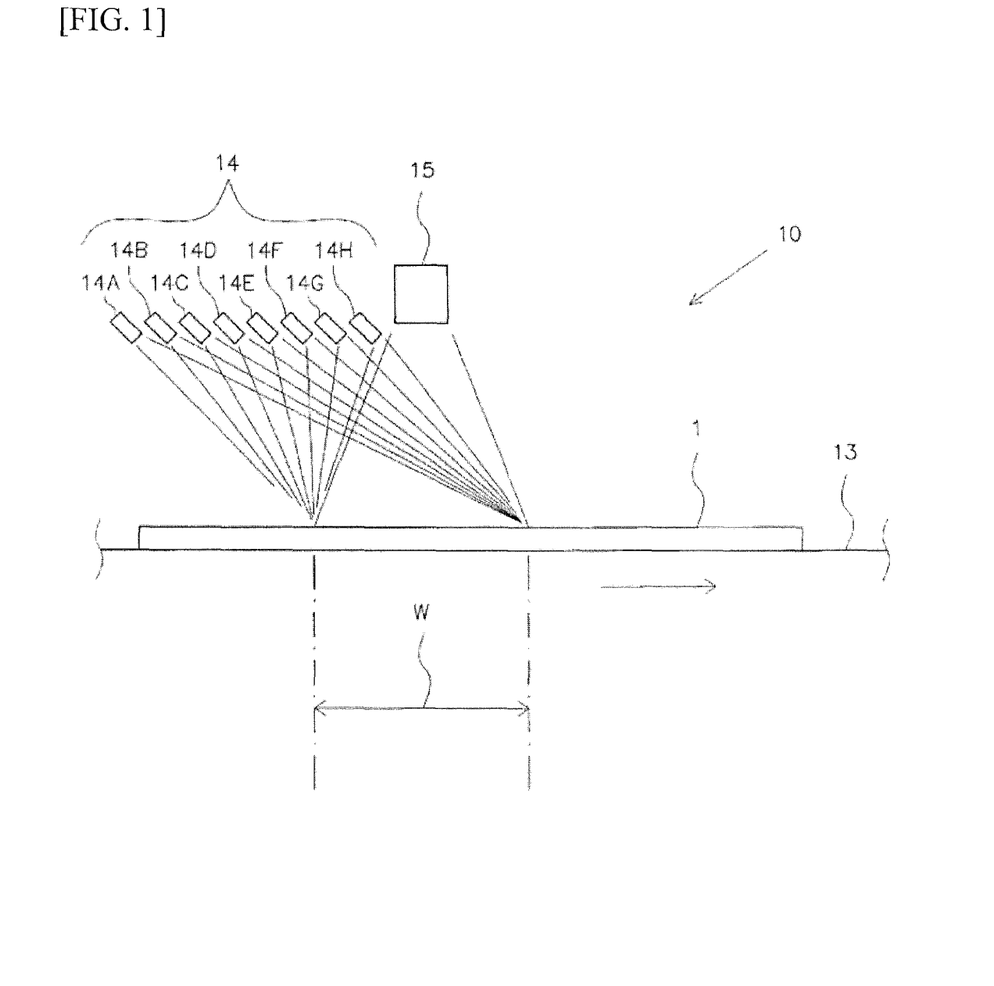
FIG. 1 is a schematic perspective view schematically illustrating a substrate inspecting device according to a first embodiment of the present invention.

Next, a description will be given in detail of the configuration of the substrate inspecting device that includes the three-dimensional measuring apparatus according to this embodiment. FIG. 1 is a schematic configuration view that schematically illustrates the substrate inspecting device 10.

Figure 3:
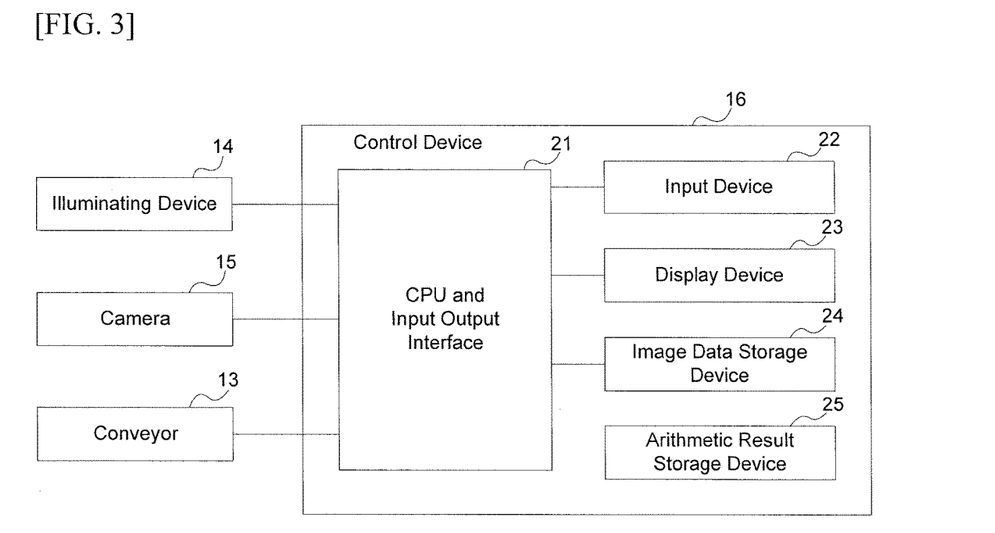
FIG. 3 is a block diagram illustrating an outline of the substrate inspecting device.

The substrate inspecting device 10 is provided with a conveyor 13 as a transporting unit to transport the printed substrate 1, an illuminating device 14 that irradiates a predetermined light from above diagonally relative to the surface of the printed substrate 1, a camera 15 as the imaging unit that images the printed substrate 1 that is irradiated by the light, and a control device 16 for executing various control, image processing, and arithmetic processing in the substrate inspecting device 10 (see FIG. 3).

A motor, not illustrated, is provided in the conveyor 13, and the printed substrate 1 placed on the conveyor 13 is continuously conveyed at a constant speed in a predetermined direction (right direction in FIG. 1) by the motor that is drive controlled by the control device 16. Accordingly, the imaging scope W of the camera 15 relatively travels in the opposite direction (left direction in FIG. 1) relative to the printed substrate 1.

The illuminating device 14 is provided with eight lights. Specifically, a first light 14A to eighth light 14H are provided.

The first light 14A and the second light 14B are provided with a commonly known liquid crystal optical shutter and are configured so that a light pattern having a banded (sinusoidal) light intensity distribution can be irradiated on the printed substrate 1 in the conveying direction. In other words, a light pattern is illuminated in which the direction of the bands is orthogonal to the conveying direction of the printed substrate 1.

However, the luminance thereof is different for the light pattern irradiated from the first light 14A and for the light pattern illuminated from the second light 14B. Specifically, the luminance of the light pattern of the first light 14A is set to a first luminance that is comparatively bright and which corresponds to the "background region" described above for the "dark portion." Meanwhile, the luminance of the light pattern of the second flight 14B is set to a second luminance that is darker than the first luminance and which corresponds to the "solder print region" described above for the "bright portion."

The third light 14C and the fourth light 14D, are configured so that a red uniform light having a constant light intensity can be irradiated across the entire scope. Similar to above, a configuration is provided in which a red uniform light of the first luminance is irradiated from the third light 14C, and a red uniform light of the second luminance is irradiated from the fourth light 14D.

The fifth light 14E and the sixth light 14F, are configured so that a green uniform light having a constant light intensity can be irradiated across the entire scope. Similar to above, a configuration is provided in which a green uniform light of the first luminance is irradiated from the fifth light 14E, and a green uniform light of the second luminance is irradiated from the sixth light 14F.

The seventh light 14G and the eighth light 14H, are configured so that a blue uniform light having a constant light intensity can be irradiated across the entire scope. Similar to above, a configuration is provided in which a blue uniform light of the first luminance is irradiated from the seventh light 14G, and a blue uniform light of the second luminance is irradiated from the eighth light 14H.

Note that from among the first light 14A to the eighth light 14H, one of either the first light 14A or the second flight 14B correspond to the first illuminating unit in this embodiment, and the other of the first light 14A or the second flight 14B as well as the third light 14C to the eighth light 14H correspond to the second illuminating unit. Accordingly, the light pattern illuminated by the other of the first light 14A or the second flight 14B as well as the uniform light irradiated by the third light 14C to the eighth light 14H, corresponds to the second light in this embodiment.

A monochrome CCD camera that uses a CCD sensor as the imaging element is used as the camera 15. Of course, the camera 15 is not limited to this. For example, a camera or the like that uses a CMOS sensor as the imaging element may also be used.

The image data imaged by the camera 15 is input into the control device 16 in the form of a digital signal after having been converted to a digital signal internally within the camera 15. Further, the control device 16 executes image processing, three-dimensional measurement processing, inspection processing, and the like, based on the image data.

Next, a detailed description will be given of the electrical configuration of the control device 16 with reference to FIG. 3. FIG. 3 is a block diagram illustrating an outline of the substrate inspecting device 10.

As illustrated in FIG. 3, the control device 16 is provided with a CPU and input output interface 21 that administers overall control of the substrate inspecting device 10; an input device 22 as input unit configured of a keyboard, mouse, or touch panel; a display device 23 as display unit having a display screen composed of a CRT, liquid crystal, or the like; an image data storage device 24 for storing image data imaged by the camera 15; and an arithmetic result storage device 25 for storing various arithmetic results such as the three-dimensional measurement result obtained based on the image data. Note that each of these devices 22 to 25 is electrically connected to the CPU and input output interface 21.

Next, detailed descriptions will be given for various processes such as the three-dimensional measurement process executed by the substrate inspecting device 10.

The control device 16 continuously conveys the printed substrate 1 at a constant speed by controlling the drive of the conveyor 13. Further, the control device 16 control the drive of the illuminating device 14 and the camera 15 based on signals from an encoder not illustrated provided on the conveyor 13.

More specifically, for each predetermined amount Δx that the printed substrate 1 is conveyed, which is to say for each predetermined time Δt that elapses, a light irradiating from the illuminating device 14 switches in a predetermined order while the printed substrate 1 irradiated by that light is imaged by the camera 15. In this embodiment, the predetermined amount Δx is set to a distance that equates to a phase $\pi/8^{th}$ (22.5° portion) of the light pattern irradiated from the first light 14A and the second flight 14B. Further, the imaging scope W of the camera 15 is set to a length equivalent to a phase $2\pi$ portion (360° portion) of the light pattern.

Figure 4:
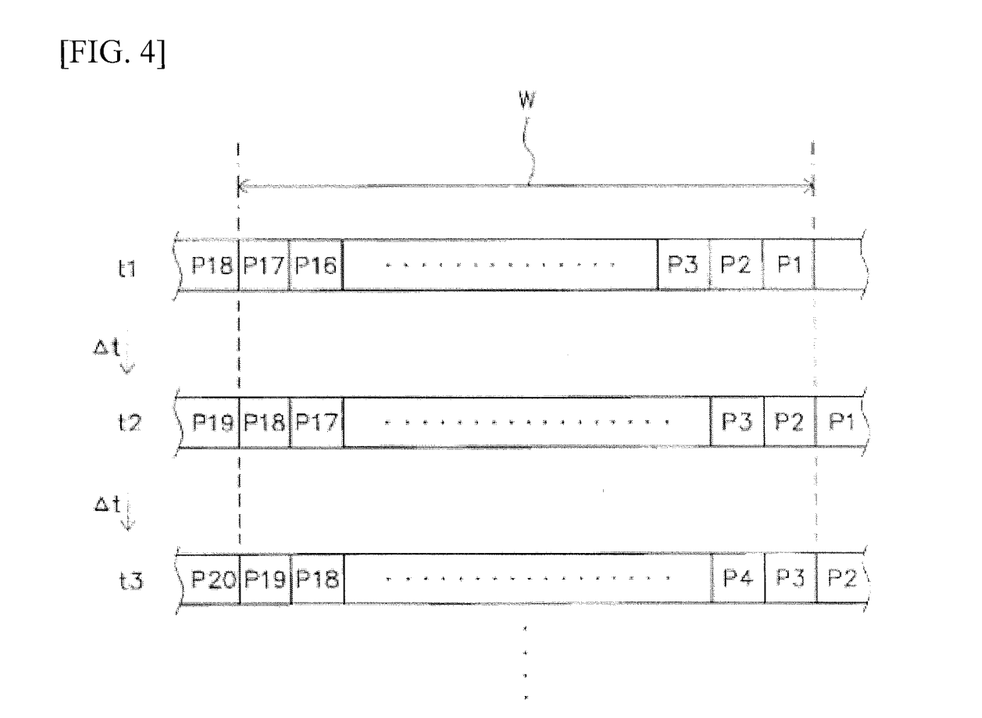
FIG. 4 is a schematic diagram for explaining a relationship between an imaging scope of a camera that changes with the passage of time and coordinate positions on a printed substrate.
Figure 5:
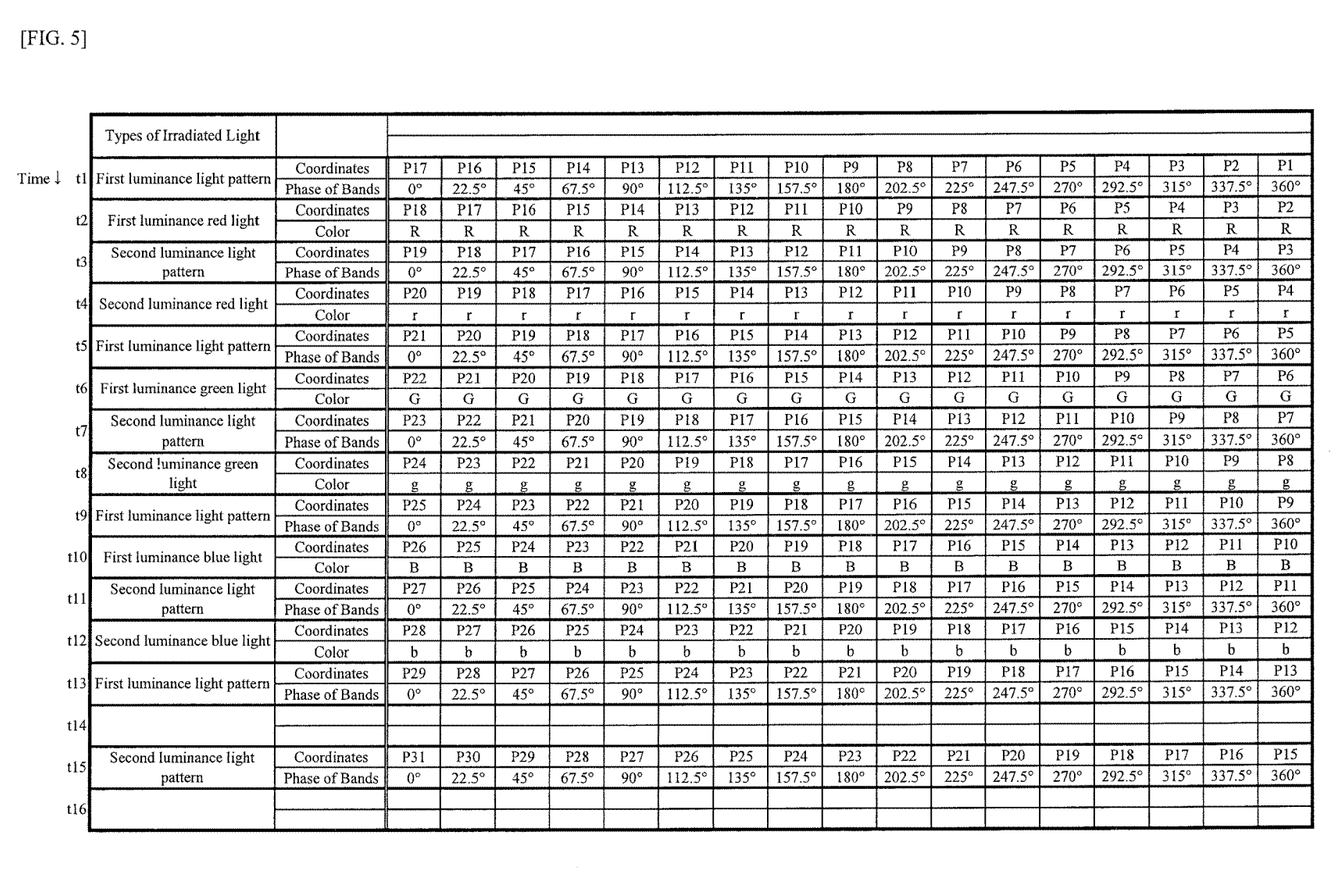
FIG. 5 is a correspondence table for explaining types of irradiated light that change with the passage of time and aspects of irradiated light in coordinate positions on a printed substrate.

Here, a detailed description will be given of a specific example for the relationship between the light irradiated from the irradiating device 14 and the imaging scope W of the camera 15. FIG. 4 is a schematic diagram for explaining a relationship between the imaging scope W of the camera 15 that relatively moves with the passage of time and the coordinate positions on a printed substrate 1. FIG. 5 is a correspondence table for explaining types of irradiated light that change with the passage of time and aspects of irradiated light (phases and the like of a light pattern) in coordinate positions on a printed substrate.

As illustrated in FIG. 4 and FIG. 5, a light pattern of the first luminance is illuminated from the first light 14A onto a printed substrate 1 in a predetermined imaging timing t1. At such time, a scope that corresponds to the coordinates P1 to P17 in the conveying direction (X direction) thereof is positioned within the imaging scope W of the camera 15 from among the printed substrates 1. In other words, in the imaging timing t1, image data is acquired for the scope between coordinates P1 to P17 on the surface of the printed substrates 1 irradiated by the light pattern having the first luminance. Note that for the direction that is orthogonal to the conveying direction (Y direction), the entire scope for the Y direction of the printed substrate 1 is included in the imaging scope of the camera 15 and there is no difference in the type or aspect of irradiated light for the coordinate positions in the Y direction in the same coordinate directions as the X direction (same hereinafter).

As illustrated in FIG. 5, in the imaging timing t1, the phases for the light pattern irradiated onto the printed substrate 1 is "0°" at coordinate P17, "22.5°" at coordinate P16, "45°" at coordinate P15, . . . , and "360°" at coordinate P1 so that image data can be acquired at phases of the light pattern at every "22.5°" for coordinates P1 to P17.

In the imaging timing t2 in which the predetermined time Δt has elapsed from the imaging timing t1, the red uniform light of the first luminance is irradiated from the third light 14C onto the printed substrate 1. At such time, a scope that corresponds to coordinates P2 to P18 of the printed substrate 1 is positioned in the imaging scope W of the camera 15, and image data of that scope is acquired. Note that the designation of the "R" on each coordinate position in FIG. 5 indicates that the light irradiated in that position is the "red uniform light of the first luminance."

In the imaging timing t3 in which the predetermined time Δt has elapsed from the imaging timing t2, the light pattern of the second luminance is irradiated from the second light 14B onto the printed substrate 1. At such time, a scope that corresponds to coordinates P3 to P19 of the printed substrate 1 is positioned in the imaging scope W of the camera 15, and image data of that scope is acquired.

In the imaging timing t4 in which the predetermined time Δt has elapsed from the imaging timing t3, the red uniform light of the second luminance is irradiated from the fourth light 14D onto the printed substrate 1. At such time, a scope that corresponds to coordinates P4 to P20 of the printed substrate 1 is positioned in the imaging scope W of the camera 15, and image data of that scope is acquired. Note that the designation of the "r" on each coordinate position in FIG. 5 indicates that the light irradiated in that position is the "red uniform light of the second luminance."

In the imaging timing t5 in which the predetermined time Δt has elapsed from the imaging timing t4, the light pattern of the first luminance is irradiated from the first light 14A onto the printed substrate 1. At such time, a scope that corresponds to coordinates P5 to P21 of the printed substrate 1 is positioned in the imaging scope W of the camera 15, and image data of that scope is acquired.

In the imaging timing t6 in which the predetermined time Δt has elapsed from the imaging timing t5, the green uniform light of the first luminance is irradiated from the fifth light 14E onto the printed substrate 1. At such time, a scope that corresponds to coordinates P6 to P22 of the printed substrate 1 is positioned in the imaging scope W of the camera 15, and image data of that scope is acquired. Note that the designation of the "G" on each coordinate position in FIG. 5 indicates that the light irradiated in that position is the "green uniform light of the first luminance."

In the imaging timing t7 in which the predetermined time Δt has elapsed from the imaging timing t6, the light pattern of the second luminance is irradiated from the second light 14B onto the printed substrate 1. At such time, a scope that corresponds to coordinates P7 to P23 of the printed substrate 1 is positioned in the imaging scope W of the camera 15, and image data of that scope is acquired.

In the imaging timing t8 in which the predetermined time Δt has elapsed from the imaging timing t7, the green uniform light of the second luminance is irradiated from the sixth light 14F onto the printed substrate 1. At such time, a scope that corresponds to coordinates P8 to P24 of the printed substrate 1 is positioned in the imaging scope W of the camera 15, and image data of that scope is acquired. Note that the designation of the "g" on each coordinate position in FIG. 5 indicates that the light irradiated in that position is the "green uniform light of the second luminance."

In the imaging timing t9 in which the predetermined time Δt has elapsed from the imaging timing t8, the light pattern of the first luminance is irradiated from the first light 14A onto the printed substrate 1. At such time, a scope that corresponds to coordinates P9 to P25 of the printed substrate 1 is positioned in the imaging scope W of the camera 15, and image data of that scope is acquired.

In the imaging timing t10 in which the predetermined time Δt has elapsed from the imaging timing t9, the blue uniform light of the first luminance is irradiated from the seventh light 14G onto the printed substrate 1. At such time, a scope that corresponds to coordinates P10 to P26 of the printed substrate 1 is positioned in the imaging scope W of the camera 15, and image data of that scope is acquired. Note that the designation of the "B" on each coordinate position in FIG. 5 indicates that the light irradiated in that position is the "blue uniform light of the first luminance."

In the imaging timing t11 in which the predetermined time Δt has elapsed from the imaging timing t10, the light pattern of the second luminance is irradiated from the second light 14B onto the printed substrate 1. At such time, a scope that corresponds to coordinates P11 to P27 of the printed substrate 1 is positioned in the imaging scope W of the camera 15, and image data of that scope is acquired.

In the imaging timing t12 in which the predetermined time Δt has elapsed from the imaging timing t11, the blue uniform light of the second luminance is irradiated from the eighth light 14H onto the printed substrate 1. At such time, a scope that corresponds to coordinates P12 to P28 of the printed substrate 1 is positioned in the imaging scope W of the camera 15, and image data of that scope is acquired. Note that the designation of the "b" on each coordinate position in FIG. 5 indicates that the light irradiated in that position is the "blue uniform light of the second luminance."

In the imaging timing t13 in which the predetermined time Δt has elapsed from the imaging timing t12, the light pattern of the first luminance is irradiated from the first light 14A onto the printed substrate 1. At such time, a scope that corresponds to coordinates P13 to P29 of the printed substrate 1 is positioned in the imaging scope W of the camera 15, and image data of that scope is acquired.

In the imaging timing t14 in which the predetermined time Δt has elapsed from the imaging timing t13, irradiating from the illuminating device 14 and imaging by the camera 15 are not performed.

In the imaging timing t15 in which the predetermined time Δt has elapsed from the imaging timing t14, the light pattern of the second luminance is irradiated from the second light 14B onto the printed substrate 1. At such time, a scope that corresponds to coordinates P15 to P31 of the printed substrate 1 is positioned in the imaging scope W of the camera 15, and image data of that scope is acquired.

In the imaging timing t16 in which the predetermined time Δt has elapsed from the imaging timing t15, irradiating from the illuminating device 14 and imaging by the camera 15 are not performed.

In the timing in which the predetermined time Δt has elapsed from the imaging timing t16, a process similar to the process of the imaging timing t1 described above is performed again. Thereafter, a process similar to the process of the imaging timing t1 to t16 described above is repeated.

In this manner, data for the entire printed substrate 1 can be obtained, and positioning processing is executed to position coordinate positions for each image data (see FIG. 6). A function for executing such process configures the positioning unit in this embodiment. FIG. 6 is a table schematically illustrating when coordinate positions of a plurality of image data that were acquired during the imaging timings t1 to t16 are aligned.

Figure 7:
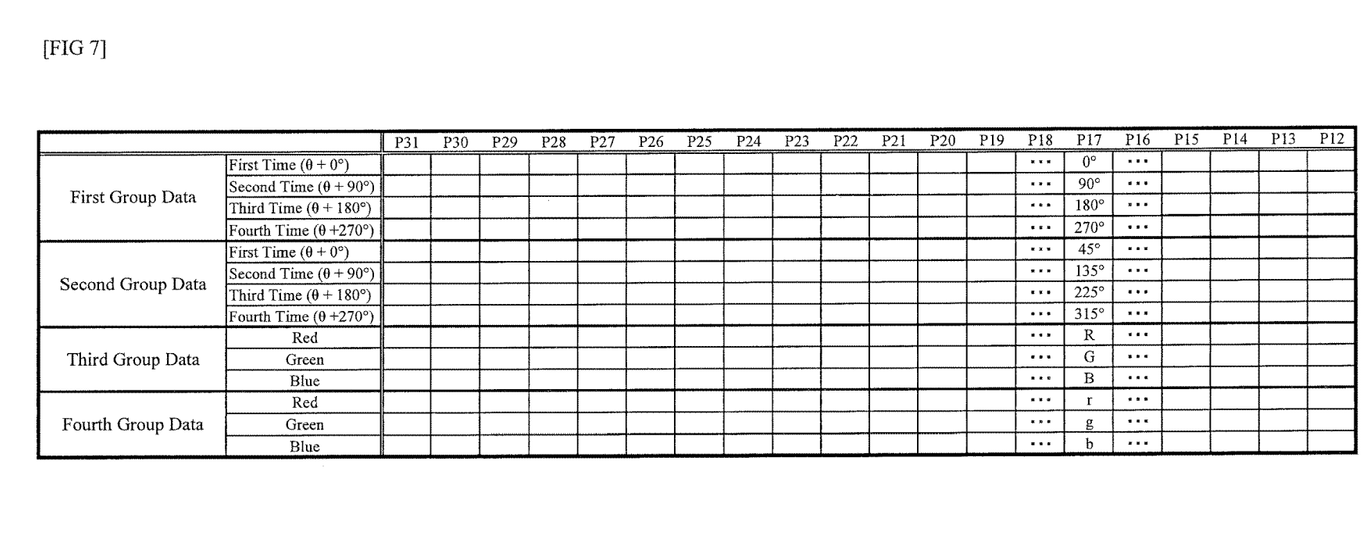
FIG. 7 is a table schematically illustrating when various data pertaining to coordinate positions on the printed substrate are organized and sorted according to each type of category.

Subsequently, after compiling the various data that pertains to the same coordinate positions of the plurality of image data according to the coordinate positions and organizing by preset groups, is stored in the arithmetic result storage device 25 (see FIG. 7). FIG. 7 is a table schematically illustrating when various data pertaining to coordinate positions on the printed substrate 1 are organized and sorted according to preset groups. However, FIG. 7 illustrates an example of only the portion that pertains to coordinate P17.

In this embodiment, for each coordinate position of the printed substrate 1, a first group data made up of four parts of data where the phases of the light pattern are offset by 90° each imaged under a light pattern of the first luminance, a second group data made up of four parts of data where the phases of the light pattern are offset by 90° each imaged under a light pattern of the second luminance, a third group data made up of luminance data of color components of three colors imaged under uniform light of each color component of red, green, and blue of the first luminance, and a fourth group data made up of luminance data of color components of three colors imaged under uniform light of each color component of red, green, and blue of the second luminance.

The processing function for acquiring one of either the first group data or the second group data configures the first image data acquiring unit in this embodiment, and the processing function for acquiring the other of the first group data or the second group data as well as the third group data and the fourth group data configures the second image data acquiring unit.

Next, the control device 16 executes various processes according to the groups based on each group data.

More specifically, height measuring is performed for each coordinate by a commonly known phase shift method described in the background technology based on the first group data. Furthermore, repeating processing for each coordinate calculates all height data for the printed substrate 1, and it is stored in the arithmetic result storage device 25 as three-dimensional data (hereinafter referred to as first three-dimensional data) of the printed substrate 1.

Similarly, height measuring is performed for each coordinate by a commonly known phase shift method based on the second group data. Furthermore, repeating processing for each coordinate calculates all height data for the printed substrate 1, and it is stored in the arithmetic result storage device 25 as three-dimensional data (hereinafter referred to as second three-dimensional data) of the printed substrate 1.

Further, color image data (hereinafter referred to as first color image data) of the entire printed substrate 1 having each color component of red, green, and blue is generated based on the third group data and is stored in the arithmetic result storage device 25.

Similarly, color image data (hereinafter referred to as second color image data) of the entire printed substrate 1 having each color component of red, green, and blue is generated based on the fourth group data and is stored in the arithmetic result storage device 25.

The processing function for acquiring one of either the first three-dimensional data or the second three-dimensional data configures the three-dimensional measuring unit in this embodiment, and the processing function for acquiring the other of the first three-dimensional data or the second three-dimensional data as well as the first color image data and the second color image data configures the specific process executing unit.

Subsequently, color information for each pixel according to each color image data is discriminated to extract various measuring target regions. For example, a range of "white" pixels are extracted from the second color image data as the solder print region, a range of "red" pixels are extracted from the first color image data as an electrode region (background region) where the electrode pattern 3 is exposed, and a range of "green" pixels are extracted as the substrate region (background region) where the base substrate 2 or the resist film 5 is exposed.

Next, determining the acceptability of the printed state of the cream solder 4 is performed based on the measured results obtained as described above. Specifically, if a print range of the cream solder 4 is detected to be higher than a predetermined length from a height reference plane, the area of the region within this range is calculated. Further, the area is determined by comparing to a reference value set in advance, and the acceptability of the printed state of the cream solder 4 is determined depending on whether the comparison results are within the allowable range.

When the determination process is being performed in this embodiment, the value of the first three-dimensional data is adopted for the solder print region extracted from the second color image data, and the value of the second three-dimensional data is adopted for the background region that becomes the height reference plane.

As described above, in this embodiment, imaging a plurality of times under a light pattern of the second luminance for the purpose of taking a three dimensional measurement according to a phase shift method and imaging under a uniform light of each color component of the first luminance and the second luminance for the purpose of acquiring luminance image data is performed during the time that imaging of a plurality of times under a light pattern of the first luminance for the purpose of taking a three dimensional measurement according to a phase shift method is performed.

In other words, in addition to acquiring image data for three-dimensional measuring, all of the image data required for performing three-dimensional measuring according to the phase shift method is acquired without extending the required time, and image data used for other purposes different from three-dimensional measuring can be acquired separately.

As a result, combining a plurality of various types of measurements is made possible when performing three-dimensional measuring using a phase shift method, and suppression of a reduction in measurement efficiency as well as improving, and the like, of measurement accuracy can be achieved.

Furthermore, switching the luminance of irradiated light to separately perform imaging according to a luminance suited to the solder print region (bright portion) and imaging according to a luminance suited to the background region (dark portion), allows the generation of various problems based on differences in light and dark areas on the printed substrate 1 to be suppressed.

Note that the present invention is not limited to the content described in the embodiments given above, and that, for example, the following may also be implemented. Of course, other application examples and modified examples not given as examples herein are also possible.

(a) In the embodiments described above, a specific case is given where the printed circuit board 1 is measured in which the cream solder 4 is "white," the electrode pattern 3 is "red," and the base substrate 2 and the resist film 5 are "green," but the configuration is not limited to this, and other specific cases may be given, for example, of measuring printed substrates having different configurations such as a printed substrate where the base substrate 2 is black or gray being relatively near black, or white or gray being relatively near white, and the like.

(b) In the embodiments described above, the three-dimensional measuring device is specifically the substrate inspecting device 10 that measures the height of the cream solder 4 that is print formed on the printed substrate 1, but the configuration is not limited to this, and other specific configurations may be given for measuring the height of other things such as, for example, a solder bump printed on a substrate, electronic components mounted on a substrate, and the like.

(c) In the phase shift method of the embodiments described above, a configuration is given where the phases of the light pattern change at a pitch of one fourth, but the configuration is not limited to this, and a configuration may be given in which the phases of the light pattern change at a pitch of one third.

(d) In the embodiments described above, a configuration is given in which color image data is created from luminance data of color components of three colors imaged under uniform light of each color component of red, green, and blue, but the configuration is not limited to this, and a configuration may be given in which color image data is acquired by irradiating, for example, white uniform light.

(e) In the embodiments described above, color image data is used to perform an extraction process for various measuring target regions, but instead of or in addition to this, it may be used for other purposes. For example, a configuration may be given in which the color image data is used for mapping the three-dimensional data obtained by three-dimensional measuring. With such configuration, variable density of the measured object can be expressed thereby allowing a texture of the three-dimensional image to be enhanced. As a result, the shape of the measured object can be easily ascertained in a moment, thereby enabling the time required for verification work to be significantly reduced.

(f) The configuration of the illuminating device 14 is not limited to the embodiment described above. For example, a configuration may be given that uses a single unit for the first light 14A and the second light 14B and changes the luminance each time.

(g) In the embodiments described above, a configuration is given where imaging a plurality of times under a light pattern of the second luminance for the purpose of taking a three dimensional measurement according to a phase shift method and imaging under a uniform light of each color component of the first luminance and the second luminance for the purpose of acquiring luminance image data is performed during the time that imaging of a plurality of times under a light pattern of the first luminance for the purpose of taking a three dimensional measurement according to a phase shift method is performed. However, the configuration is not limited to this, and a configuration may be given, for example, in which imaging is performed only one time under a white uniform light during the time that imaging is performed a plurality of times under a light pattern of the first luminance for the purpose of taking a three dimensional measurement according to a phase shift method.

(h) In the embodiments described above, a phase shift method is used as the three-dimensional measuring method in which a light pattern is used, but other than this, various three-dimensional measuring methods may be adopted such as a space coding method, moire method, focus method, or the like.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF NUMERICAL REFERENCES

1 . . . printed substrate, 4 . . . cream solder, 10 . . . substrate inspecting device, 13 . . . conveyor, 14 . . . illuminating device, 14A to 14H . . . light, 15 . . . camera, 16 . . . control device, 24 . . . image data storage device, 25 . . . arithmetic result storage device, P1 to P3 1 . . . coordinates, W . . . imaging scope

What is claimed is:

1. A three-dimensional measuring apparatus, comprising:
 a first irradiating unit that irradiates a light pattern onto a measured object, having a banded light intensity distribution in a conveying direction of the measured object;
 a second irradiating unit that irradiates a uniform light of a constant light intensity onto the measured object;
 an imaging unit that images the measured object irradiated by the light pattern or the uniform light; and
 a processor that:
  acquires a first plurality of image data imaged by the imaging unit under the light pattern for each predetermined amount of conveyance by the measured object;
  three dimensionally measures the object based on the acquired first plurality of image data;
  acquires a second plurality of image data imaged by the imaging unit under the uniform light, wherein one of the second plurality of image data is acquired after predetermined image data from among the first plurality of image data is imaged but before next image data is imaged; and
  executes a predetermined process based on the one of the acquired second plurality of image data,
 wherein
 the measured object is a continuously conveyed printed substrate,
 the predetermined amount of conveyance is based on a phase of the light pattern,
 the processor alternately acquires each piece of the first plurality of image data and each piece of the second plurality of image data with the first irradiating unit and the second irradiating unit, respectively, every time the measured object is conveyed by the predetermined amount of conveyance,
 the first plurality of image data comprises image data imaged under the light pattern of a first luminance value for a region other than a solder print region of the printed substrate, and image data imaged under the light pattern of a second luminance value greater than the first luminance value, wherein the second luminance value is for the solder print region, and wherein the image data imaged under the light pattern of the first luminance value and the image data imaged under the light pattern of the second luminance value are alternately acquired, and
 the second plurality of image data comprises image data imaged under the uniform light by switching a plurality of uniform lights having different colors, wherein the image data imaged under the uniform lights of the different colors are acquired in sequence during the time until the acquired first plurality of imaging data is all imaged.

2. The three-dimensional measuring apparatus according to claim 1, wherein the processor aligns coordinates between mutual image data acquired respectively at different positions in a conveying direction of the printed substrate.

3. The three-dimensional measuring apparatus according to claim 1, wherein the image data imaged under the uniform lights comprise image data imaged under the uniform lights that have the same color and different luminance values.

4. The three-dimensional measuring apparatus according to claim 1, wherein the different colors comprise red, green, and blue.

5. The three-dimensional measuring apparatus according to claim 1, wherein the predetermined amount of conveyance corresponds to $\pi/8$ and an imaging scope of the imaging unit corresponds to $2\pi$, where $\pi$ indicates the phase of the light pattern of 180 degrees.

6. A three-dimensional measuring apparatus, comprising:
a first irradiating unit that irradiates a light pattern onto a measured object, having a banded light intensity distribution in a conveying direction of the measured object;
a second irradiating unit that irradiates a uniform light of a constant light intensity onto the measured object;
an imaging unit that images the measured object irradiated by the light pattern or the uniform light; and
a processor that:
acquires a first plurality of image data imaged by the imaging unit under the light pattern for each predetermined amount of conveyance by the measured object;
uses a phase shift method to three dimensionally measure the object based on the acquired first plurality of image data;
acquires a second plurality of image data imaged by the imaging unit under the uniform light, wherein one of the second plurality of image data is acquired after predetermined image data from among the first plurality of image data is imaged but before next image data is imaged; and
executes a predetermined process based on the one of the acquired second plurality of image data,
wherein
the measured object is a continuously conveyed printed substrate,
the predetermined amount of conveyance is based on a phase of the light pattern,
the processor alternately acquires each piece of the first plurality of image data and each piece of the second plurality of image data with the first irradiating unit and the second irradiating unit, respectively, every time the measured object is conveyed by the predetermined amount of conveyance,
the first plurality of image data comprises image data imaged under the light pattern of a first luminance value for a region other than a solder print region of the printed substrate, and image data imaged under the light pattern of a second luminance value greater than the first luminance value, wherein the second luminance value is for the solder print region, and wherein the image data imaged under the light pattern of the first luminance value and the image data imaged under the light pattern of the second luminance value are alternately acquired, and
the second plurality of image data comprises image data imaged under the uniform light by switching a plurality of uniform lights having different colors, wherein the image data imaged under the uniform lights of the different colors are acquired in sequence during the time until the acquired first plurality of imaging data is all imaged.

7. The three-dimensional measuring apparatus according to claim 6, wherein the processor aligns coordinates between mutual image data acquired respectively at different positions in a conveying direction of the printed substrate.

8. The three-dimensional measuring apparatus according to claim 6, wherein the image data imaged under the uniform lights comprise image data imaged under the uniform lights that have the same color and different luminance values.

9. The three-dimensional measuring apparatus according to claim 6, wherein the different colors comprise red, green, and blue.

10. The three-dimensional measuring apparatus according to claim 6, wherein the predetermined amount of conveyance corresponds to $\pi/8$ and an imaging scope of the imaging unit corresponds to $2\pi$, where $\pi$ indicates the phase of the light pattern of 180 degrees.

* * * * *